(12) United States Patent
Wakuda et al.

(10) Patent No.: US 7,686,891 B2
(45) Date of Patent: Mar. 30, 2010

(54) METHOD AND APPARATUS FOR COLLECTING CHEMICALS FROM SEMICONDUCTOR WAFER

(75) Inventors: Mariko Wakuda, Nagasaki (JP); Ichiro Sato, Nagasaki (JP)

(73) Assignee: Sumco TechXIV Corporation, Nagasaki (JP)

( * ) Notice: Subject to any disclaimer, the term of this patent is extended or adjusted under 35 U.S.C. 154(b) by 382 days.

(21) Appl. No.: 11/630,810

(22) PCT Filed: Jun. 28, 2005

(86) PCT No.: PCT/JP2005/011835

§ 371 (c)(1),
(2), (4) Date: Dec. 27, 2006

(87) PCT Pub. No.: WO2006/001451

PCT Pub. Date: Jan. 5, 2006

(65) Prior Publication Data

US 2007/0204881 A1    Sep. 6, 2007

(30) Foreign Application Priority Data

Jun. 28, 2004    (JP) .............................. 2004-190031

(51) Int. Cl.
*B08B 1/04* (2006.01)
(52) U.S. Cl. .......................... 134/34; 438/14
(58) Field of Classification Search ........................ None
See application file for complete search history.

(56) References Cited

U.S. PATENT DOCUMENTS

2001/0039119 A1* 11/2001 Kishimoto .................. 438/690

FOREIGN PATENT DOCUMENTS

JP    10-092889    4/1998

(Continued)

OTHER PUBLICATIONS

Machine Translation of JP 07-159293 to Takizawa, published Jun. 23, 1995.*

(Continued)

*Primary Examiner*—Michael Kornakov
*Assistant Examiner*—Ryan Coleman
(74) *Attorney, Agent, or Firm*—Husch Blackwell Sanders LLP Welsh & Katz

(57) ABSTRACT

An apparatus and a method are provided for accurately analyzing and evaluating a degree of contamination on a chamfered part without mixing impurities from parts other than the chamfered part into chemicals. At a position in which, on a front plane flat part of a semiconductor wafer, a boundary region bordering the chamfered part can come into contact with the chemicals, a radius direction position of the chemicals (a distance between a chemicals center and a wafer center) is determined, scanning is performed in a circumference direction, and the chemicals including impurities are collected. Then, at a position that can be brought into contact with the both chamfered part of the semiconductor wafer and the boundary region, a radius direction position of the chemicals is determined, scanning is performed in the circumference direction and the chemicals including impurities are collected. A liquid drop holder is, for instance, relatively rotated in the circumference direction from a desired start point on the circumference of the semiconductor wafer to a finish point.

1 Claim, 9 Drawing Sheets

FOREIGN PATENT DOCUMENTS

| | | |
|---|---|---|
| JP | 11-204604 | 7/1999 |
| JP | 2000-077492 | 3/2000 |
| JP | 2002-134576 | 5/2002 |
| JP | 2002-289660 | 10/2002 |
| JP | 2005-109292 | 4/2005 |

OTHER PUBLICATIONS

Machine Translation of JP 2002-134576 by Yamagami, published May 10, 2002.*

* cited by examiner

US 7,686,891 B2

METHOD AND APPARATUS FOR COLLECTING CHEMICALS FROM SEMICONDUCTOR WAFER

TECHNICAL FIELD

The present invention relates to a semiconductor wafer and particularly to a method and a device for collecting impurities on a chamfered part of the semiconductor wafer with chemicals.

BACKGROUND ART

Among methods for analyzing an amount and concentration of impurities such as metals that have adhered to a silicon wafer surface and evaluating a degree of contamination, there exists a method of analysis and evaluation through collecting chemicals.

In methods of analysis and evaluation through collecting chemicals the device and method to be used are determined according to the region of the silicon wafer.

When the front plane flat part of the silicon wafer is analyzed and evaluated a liquid drop automatic scanning device shown in FIGS. 1A and 1B is used.

FIG. 1A shows a top surface view of the liquid drop automatic scanning device, and FIG. 1B shows a perspective view of the liquid drop automatic scanning device.

As shown in FIGS. 1A and 1B the back plane 10a of the silicon wafer 10 is held and at the same time supported so that it can rotate freely by a fastener not shown in the drawings so that it lies on a horizontal position. On the side of the front plane 10a of the silicon wafer 10, a liquid drop supply arm 20 and a liquid drop holder 30 are disposed. The liquid drop holder 30 is fastened to the tip of the liquid drop supply arm 20 through a vacuum. The liquid drop supply arm 20 has a degree of movability to move the liquid drop holder 30 from the center 10c of the silicon wafer 10 in a radius direction A of the wafer 10. Additionally, the height of the liquid drop supply arm 20 is adjusted to a predetermined height and a liquid drop discharge opening 30a of the liquid drop holder 30 is separated from the front plane 10a of the silicon wafer 10 at only a sufficient predetermined distance to retain chemicals 40. With a controller 50 the liquid drop supply arm 20 is drive-controlled, and a rotation drive source of the silicon wafer 10 is drive-controlled at the same time as the liquid drop holder 30 moves in the radius direction A, and thus the silicon wafer 10 rotates. A tank 60 for collecting the chemicals 40 is provided in a location separate from the silicon wafer 10.

FIGS. 2A through 2D explain means for the liquid drop holder 30 to retain the chemicals 40. FIG. 3 shows a perspective view of a cross section of the liquid drop holder 30.

As shown in FIGS. 2A and 2B, liquid drops 41 are supplied into the liquid drop holder 30 via the inside portion of the liquid drop supply arm 20 and are dropped in succession one drop at a time from the liquid drop discharge opening 30a onto the front plane 10a of the silicon wafer 10. Thus the chemicals 40 on the silicon wafer 10 gradually increase. When at last the chemicals 40 increases enough to reach a discharge opening R shown in FIG. 3, it becomes possible to maintain a state in which a front plane tensile force of the chemicals 40 arises and the liquid drop holder 30 causes the chemicals 40 to contact the front plane 10a of the silicon wafer 10 (FIG. 2C).

Then if the liquid drop supply arm 20 is drive-controlled and the liquid drop holder 30 is moved in a radius direction A then the chemicals 40 can be moved together with the liquid drop holder 30 in the same direction A (FIG. 2D).

Next the operation of the liquid drop automatic scanning device of FIGS. 1A and 1B will be explained.

FIG. 4A is a perspective view showing the movement of the liquid drop holder 30 in a radius direction. FIG. 4B shows the trajectory of the center 40c of the chemicals 40 on the silicon wafer 10.

If the state is reached in which the chemicals 40 is maintained by the liquid drop holder 30 as mentioned above, then the liquid drop supply arm 20 is drive-controlled by the controller 50 and thus the liquid drop holder 30 is positioned on the center 10c of the silicon wafer 10. And as shown in the same FIG. 4A, the rotation drive source is drive-controlled by the controller 50 and thus the silicon wafer 10 is rotated at a fixed speed and at the same time the liquid drop supply arm 20 is drive-controlled by the controller 50 and thus the liquid drop holder 30 is moved in a radius direction A at a predetermined speed (for example, a pitch of several mm per rotation). Thus the liquid drop holder 30 rotates relative to the silicon wafer 10 at a predetermined speed in a circumference direction $\omega$ of the silicon wafer 10 while moving at a predetermined speed in the radius direction A of the silicon wafer 10. As a result, as shown in FIG. 4B, the chemicals center 40c is scanned on the front plane 10a of the silicon wafer 10 in the circumference direction $\omega$ and forms a spiral-shaped trajectory starting from the center 10c of the silicon wafer 10.

FIG. 5A shows the trajectory of the final circuit of the chemicals center 40c. While the chemicals center 40c is scanned from the scan start point S to the scan finish point G, it advances in the radius direction A for a predetermined distance, thus the radius direction positions of the points are different.

FIG. 5B shows chemicals collecting region 42 in which impurities that contact the chemicals 40 on the front plane of the silicon wafer 10 dissolve into the chemicals 40 and the chemicals 40 including the impurities are collected, and a profile of the chemicals non-collecting region 43 outside the chemicals collecting region 42. The chemicals collecting region 42 as shown by the diagonal lines in FIG. 5B forms a shape according to the final circuit of the trajectory shown in FIG. 5A, thus various portions in the circumference direction of the silicon wafer 10 have various lengths in the radius direction.

The chemicals 40 in which impurities are dissolved is carried to the tank 60 and collected into the tank 60 while still being retained by the liquid drop holder 30. By analyzing the chemicals 40 collected in the tank 60 the degree of contamination on the front plane flat part of the silicon wafer 10 can be evaluated.

Next the device for analyzing and evaluating the chamfered part of the silicon wafer 10 will be described.

FIG. 6 shows a manual chemicals collecting device for collecting chemicals manually on the chamfered part (edge part) of the silicon wafer 10.

As shown in FIG. 6 a dedicated jig 70 is attached at the wafer center 10c of the silicon wafer 10 perpendicular to the wafer surface in the length direction. A ship-bottom shaped groove 81 is formed in a container 80 and the chemicals 40 accumulate in this grove 81. The silicon wafer 10 stands perpendicular to the container 80 and the chamfered part 15 is dipped in the chemicals 40. While maintaining the perpendicular state of the silicon wafer 10 the dedicated jig 70 is manually rotated 90 degrees, ¼ of a circuit in the circumference direction of the chamfered part 15 of the silicon wafer 10 contacts the chemicals 40, and the impurities adhered to the chamfered part 15 of this region are dissolved into the chemicals 40. FIG. 11B shows a collecting region 44 of the silicon wafer 10. An operator sets a position at which a notch 17 is formed as 0 degrees, and performs the chemicals collecting operation by verifying by sight that the dedicated jig 70 turns ¼ of a circuit (90 degrees) from the notch position (0 degrees).

The degree of contamination of the chamfered part 15 of the silicon wafer 10 can be evaluated by analyzing the chemicals 40 collected to the container 80. Note that the chemicals collecting operation is performed in a clean room.

The manual chemicals collecting device is disclosed in patent document 1 below.

Additionally in patent documents 2 and 3 below a configuration of an automatic chemicals collecting device is disclosed which comprises a retaining device and a rotating device, and automatically collects chemicals from a chamfered part (edge part) by rotating a silicon wafer 10 with the rotating device while retaining the silicon wafer 10 in a perpendicular state in the same manner as in the manual chemicals collecting device of FIG. 6 with the retaining device.

Patent Document 1: Japanese Patent Application Laid-Open No. 2000-77492
Patent Document 2: Japanese Patent Application Laid-Open No. 10-92889
Patent Document 3: Japanese Patent Application Laid-Open No. 11-204604

DISCLOSURE OF THE INVENTION

Problems to be Solved by the Invention

Next the problems in the above-mentioned prior art will be described.

According to the liquid drop automatic scanning device in FIGS. 1A and 1B and as explained in FIGS. 5A and 5B, the liquid drop center 40c forms a spiral-shaped trajectory on the final circuit, hence the chemicals collecting region 42 has a problem of instability. Thus an error can occur in the results of the analysis and evaluation of the degree of contamination on the front plane flat part of the silicon wafer 10.

The height of the liquid drop holder 30 is fixed to a height in which the chemicals 40 can be retained on the front plane flat part, hence the chemicals 40 cannot be reached to the chamfered part 15 even if the liquid drop holder 30 is moved to the chamfered part 15. Thus the analysis and evaluation of the chamfered part 15 using this liquid drop automatic scanning device cannot be performed.

In the manual chemicals collecting device of FIG. 6, there is a problem of variation in the collecting region according to the operator leading to instability of the collecting region because the collecting operation is performed by hand. Thus an error can occur in the results of the analysis and evaluation of the degree of contamination on the chamfered part 15 of the silicon wafer 10.

Additionally the analysis and evaluation of the chamfered part 15 cannot be performed accurately because a region other than the chamfered part 15 is also dipped into the chemicals since the chamfered part 15 is dipped into the chemicals 40 with the silicon wafer 10 held in a perpendicular state. This will be explained using FIG. 7.

FIG. 7 shows a cross section of the outer periphery part of the silicon wafer 10. The silicon wafer 10 is formed from a front plane flat part 11, which is the flat part on the front plane 10a, the chamfered part 15, and a back plane flat part 16, which is the flat part of the back plane 10b. The chamfered part 15 is formed from a front plane beveled part 12 having its front plane cut at a predetermined angle to the front plane flat part 11 on the front plane 10a, a straight core part 13 having a surface perpendicular to the front plane flat part 11 and the back plane flat part 16, and a back plane beveled part 14 having its back plane cut at a predetermined angle to the back plane flat part 16 on the back plane 10b.

When the silicon wafer 10 is in a perpendicular state and the chamfered part 15 is dipped in the chemicals 40, the chemicals 40 contacts the surface from the straight core part 15 to a removed location of a predetermined distance $\Delta X$. The chemicals collecting region 44 includes not only the chamfered part 15 but also the front plane flat part 11 and the back plane flat part 16. Thus the impurities adhered to the front plane flat part 11 and the back plane flat part 16 are mixed into the chemicals 40. In particular the impurities on the back plane flat part 16 include impurities unique to the back plane due to backside damage and the like which is highly dependent on the type of silicon wafer. Thus the results of the analysis and evaluation of the degree of contamination are largely influenced by the degree of contamination on the back plane 1b and the analysis and evaluation of the degree of contamination on the chamfered part 15 cannot be performed accurately.

Even though the operation is performed in a clean room, because it is a manual operation, contamination can occur due to impurities that fall into the chemicals 40 from the chemicals 40 above it leading to an error occurring in the results of the analysis and evaluation.

As collecting is performed while verifying the rotation angle by sight as described in FIG. 11B, the collecting region is limited to a region in which the angle is verifiable by sight, 90 degrees, 180 degrees, 270 degrees and 360 degrees (a complete circuit), as measured from the notch 17 (0 degrees). Thus the collecting start angle and the collecting finish angle are limited, and the collecting of the chemicals 40 can not be performed at the desired start angle and finish angle and on a desired region.

On the other hand, when the chemicals 40 of the chamfered part 15 are collected with the automatic chemicals collecting device, even if the above-mentioned problems due to performing the operation manually don't occur, because the method of dipping the silicon wafer 10 into the chemicals 40 while it is retained perpendicularly does not change, as described in FIG. 7, due to the influence of impurities from the region outside the chamfered part 15 (in particular the rear plane flat part 16) the problem cannot be avoided in which the accuracy of results of the analysis and evaluation is affected. Additionally, as the silicon wafer 10 is in a perpendicular position, the silicon wafer 10 and the device operating part are located above the chemicals 40, thus impurities from above other than the part dipped in the chemicals 40 can be mixed therein.

As mentioned above the liquid drop automatic scanning device of FIGS. 1A and 1B is a dedicated device for collecting the chemicals 40 on the front plane flat part 11, and the manual chemicals collecting device of FIG. 6 and the automatic chemicals collecting device are dedicated devices for collecting the chemicals 40 on the chamfered part 15, hence when analysis and evaluation are performed on the degree of contamination of both the front plane flat part 11 and the chamfered part 15, two devices must be set up and two silicon wafers must be provided and the operations must be performed separately. Thus the efficiency of the operation suffers because the operation requires a large amount of time and effort.

The present invention has an object of solving the above-mentioned problems.

The present invention is designed so that impurities not from the chamfered part 15 are not mixed into the chemicals 40, thus solving one of the problems by achieving good accuracy in the analysis and evaluation of the degree of contamination of the chamfered part 15.

Additionally, the present invention is designed so that all of the chemicals 40 are collected from the entire range of the front plane flat part 11, thus solving one of the problems by achieving good accuracy in the analysis and evaluation of the degree of contamination of the front plane flat part 11.

Also, the present invention provides a one-unit device that uses one silicon wafer 10 and can perform a collecting operation on the front plane flat part 11 and the chamfered part 15 in succession, solving one of the problems by raising the operation efficiency.

The present invention also solves one of the problems by allowing a desired collecting start point and collecting finish point to be set and a desired collecting region when collecting the chemicals 40 on the chamfered part 15.

Means to Solve the Problems

A first aspect of the present invention provides a chemicals collecting method for a semiconductor wafer, in which chemicals including impurities are collected by scanning the chemicals in a circumference direction in a state in which the chemicals are caused to contact a front plane of the semiconductor wafer, the method comprising:

a first step of collecting the chemicals including impurities by determining, on a front plane flat part of the semiconductor wafer, a radius direction position of the chemicals at a position where the chemicals can contact a boundary region bordering a chamfered part, and by scanning in the circumference direction; and a second step of collecting the chemicals including impurities by determining the radius direction position of the chemicals at a position where the chemicals can contact both the chamfered part and the boundary region of the semiconductor wafer, and by scanning in the circumference direction.

A second aspect of the present invention provides a chemicals collecting device for a semiconductor wafer, in which chemicals including impurities are collected by moving a liquid drop holder in a radius direction of the semiconductor wafer while rotating the liquid drop holder relative to a circumference direction of the semiconductor wafer, in a state in which the chemicals are caused to contact a front plane of the semiconductor wafer by the liquid drop holder, the device comprising:

first control means for collecting the chemicals including impurities by positioning the liquid drop holder at a radius direction position in which the chemicals can contact a boundary region bordering a chamfered part, on a front plane flat part of the semiconductor wafer, and by causing the liquid drop holder to rotate relative to the circumference direction of the semiconductor wafer; and second control means for collecting the chemicals including impurities by positioning the liquid drop holder at a radius direction position in which the chemicals can contact both the chamfered part and the boundary region of the semiconductor wafer, and by causing the liquid drop holder to rotate relative to the circumference direction of the semiconductor wafer.

A third aspect of the present invention provides the chemicals collecting device according to the second aspect of the present invention, characterized in that the second control means adjusts a distance from the liquid drop holder to the semiconductor wafer so that the chemicals cover the chamfered part.

A fourth aspect of the present invention provides the chemicals collecting device according to the second aspect of the present invention, characterized in that the second control means rotates the liquid drop holder relative to the circumference direction, from a desired start point to a finish point on a periphery of the semiconductor wafer.

According to the first to the fourth aspects of the invention and as shown in FIGS. 8A and 8B, a radius direction position of the chemicals 40 (at a distance R from a wafer center 10c of a chemicals center 40c) is determined at a position in which, on the front plane flat part 11 of the semiconductor wafer 10, the boundary region bordering the chamfered part 15 can come into contact with the chemicals 40, scanning is performed in the circumference direction ω and the chemicals 40 including impurities is collected.

Next, as shown in FIG. 9, a position in the radius direction of the chemicals 40 is determined at a position in which both the chamfered part 15 of the semiconductor wafer 10 and the boundary region 11a can come into contact with the chemicals 40, scanning is performed in a circumference direction ω, and the chemicals 40 including impurities is collected.

In the third aspect of the present invention, as shown in FIG. 9, the distance from the liquid drop holder 30 to the semiconductor wafer 10 is adjusted so that the chemicals 40 can be reached into the chamfered part 15. Specifically, the height of the liquid drop holder 30 is adjusted.

In the fourth aspect of the present invention, when scanning is performed in the circumference direction ω in FIG. 9, the liquid drop holder 30 is rotated from a desired start point S2 on the periphery of the semiconductor wafer 10 to a finish point G2 relative to the circumference direction, as shown in FIG. 11A.

A fifth aspect of the present invention provides a chemicals collecting method for a semiconductor wafer, in which chemicals including impurities are collected by scanning the chemicals in a circumference direction in a state in which the chemicals contact a front plane of the semiconductor wafer, the method comprising:

a first step of collecting the chemicals including impurities by scanning in the circumference direction while causing the chemicals to move in a radius direction from a center of the wafer to, on a front plane flat part of the semiconductor wafer, a boundary region bordering a chamfered part; and a second step of collecting the chemicals including impurities by fixing a radius direction position of the chemicals at a point in time when the radius direction position of the chemicals is reached at a position where the chemicals can contact the boundary region bordering the chamfered part, and by scanning in the circumference direction.

According to the fifth aspect of the present invention, as shown is FIGS. 4A and 4B, the chemicals 40 including impurities are collected by scanning in the circumference direction ω while causing the chemicals 40 to move in the radius direction A from the wafer center 10c to, on the front plane flat part 11 of the semiconductor wafer 10, the boundary region bordering the chamfered part 15. Next, as shown in FIGS. 8A and 8B, the position in the radius direction of the chemicals 40 is fixed (the distance R is constant) at the point in time in which the position in the radius direction of the chemicals 40 reaches the position in which the chamfered part 15 and the boundary region 11a can come into contact with the chemicals 40, scanning is performed in the circumference direction ω, and the chemicals 40 including impurities are collected.

Effects of the Invention

According to the first to the fourth aspects of the present invention, as shown in FIG. 10, the chemicals 40 span the entire region in the circumference direction of the silicon wafer 10 and contacts both the chamfered part 15 and the boundary region 11a (a chemicals collecting region 46), and impurities adhered to the chamfered part 15 are dissolved into the chemicals 40. At this point, the impurities adhered to the boundary region 11a have already been collected through the aforementioned step, in other words the last collecting step of the front plane flat part 11 shown in FIG. 8A. Accordingly, the impurities on the boundary region 11a do not mix into the chemicals 40 even if a portion of the chemicals 40 is in contact with the boundary region 11a as in FIG. 10, and only the impurities adhered to the chamfered part 15 dissolve into the chemicals 40. As shown above, only the impurities on the chamfered part 15 of the silicon wafer 10 are dissolved into the chemicals 40, hence the analysis and evaluation of the degree of contamination of the chamfered part 15 can be performed with great accuracy.

In the first to the fourth aspects of the present invention one liquid drop automatic scanning device (FIGS. 1A and 1B) is used and one silicon wafer 10 is used, thus chemicals collecting can be performed successively on both the front plane flat part 11 and the chamfered part 15, resulting in a dramatic improvement of the operation efficiency.

According to the fourth aspect of the present invention, as shown in FIG. 11A, when collecting the chemicals 40 on the chamfered part 15, the collecting start point and the collecting finish point can be set at desired points and collecting can be performed on a desired region 46, hence the degree of flexibility in indicating the chemicals collecting region is improved.

According to the fifth invention, the chemicals 40 can be completely collected without exception on the entire range of the front plane flat part 11, hence the analysis and evaluation of the degree of contamination of the front plane flat part 11 can be performed with good accuracy.

Furthermore, according to the first to the fourth aspects of the present invention, analysis and evaluation of the degree of contamination can be performed on both the front plane flat part 11 and the chamfered part 15 using one silicon wafer 10, hence the accuracy of the analysis and evaluation is higher compared to the prior art in which the analysis and evaluation of the degree of contamination of the wafer is performed using a plurality of wafers, one each for the front plane flat part 11 and the chamfered part 15.

BEST MODE FOR CARRYING OUT THE INVENTION

Below a chemicals collecting method and device for a semiconductor wafer relating to the present invention and the best mode for carrying out the invention is explained while referring to the drawings.

In the present exemplary embodiment a liquid drop automatic scanning device shown in FIGS. 1A and 1B is used. A collecting operation of a front plane flat part 11 and a collecting operation of a chamfered part 15 are performed in succession using one silicon wafer 10 by the liquid drop automatic scanning device shown in FIGS. 1A and 1B.

FIG. 1A shows a top surface view of the liquid drop automatic scanning device, and FIG. 1B shows a perspective view of the liquid drop automatic scanning device.

As shown in these FIGS. 1A and 1B, a back plane 10a of the semiconductor wafer 10 is held in a horizontal state and at the same time supported rotatably by a fastener not shown in the drawings. A liquid drop supply arm 20 and a liquid drop holder 30 are disposed on a front plane 10a side of the silicon wafer 10. The liquid drop holder 30 is vacuum fastened to the tip of the liquid drop supply arm 20. The liquid drop supply arm 20 has a degree of flexibility in moving the liquid drop holder 30 from a center 10c of the silicon wafer 10 in a radius direction A of the same wafer 10. Also, the liquid drop supply arm 20 has a degree of flexibility in moving the liquid drop holder 30 in the height direction H. A distance from the front plane 10a of the silicon wafer 10 to a chemicals discharge opening 30a of the liquid drop holder 30 is adjusted to a desirable length by adjusting the height of the liquid drop holder 30.

With a controller 50 the liquid drop supply arm 20 is drive-controlled and the liquid drop holder 30 moves in the radius direction A and at the same time moves in the height direction H. Also a rotation drive source of the silicon wafer 10 is drive-controlled by the controller 50 and thus the silicon wafer 10 rotates. A tank 60 for collecting the chemicals 40 is provided in a location removed from the silicon wafer 10.

FIGS. 2A to 2D are drawings that explain the process of the liquid drop holder 30 retaining the chemicals 40. FIG. 3 is a perspective view of a cross section of the liquid drop holder 30.

As shown in FIGS. 2A and 2B, liquid drops 41 are supplied into the liquid drop holder 30 via an inside portion of the liquid drop supply arm 20 and are dropped in succession one drop at a time from a liquid drop discharge opening 30a onto the front plane 10a of the silicon wafer 10. Thus chemicals 40 on the silicon wafer 10 gradually increase. When at last the chemicals 40 increase enough to reach a discharge opening R shown in FIG. 3, it becomes possible to maintain a state in which a front plane tensile force of the chemicals 40 arises and the liquid drop holder 30 causes the chemicals 40 to contact the front plane 10a of the silicon wafer 10 (FIG. 2C).

Then if the liquid drop supply arm 20 is drive-controlled and the liquid drop holder 30 is moved in a radius direction A then the chemicals 40 can be moved together with the liquid drop holder 30 in the same direction A (FIG. 2D).

Next the operation of the liquid drop automatic scanning device of FIGS. 1A and 1B will be explained.

First Embodiment (Collecting Performed on the Front Plane Flat Part 11)

FIG. 4A is a side plane view showing the movement of the liquid drop holder 30 in a radius direction. FIG. 4B shows the trajectory of the center 40c of the chemicals 40 on the silicon wafer 10.

When performing chemicals collecting on the front plane flat part 11 the height of the liquid drop holder 30 is adjusted to a height in which the chemicals 40 can be retained in a state in which it contacts the front plane flat part 11.

If a state has been reached in which the chemicals 40 can be retained with the liquid drop holder 30 through the process shown in FIGS. 2A to 2C, the liquid drop supply arm 20 is drive-controlled by the controller 50 and the liquid drop holder 30 is positioned at the center 10c of the silicon wafer 10. As shown in FIG. 4A the rotation drive source is drive-controlled by the controller 50 and the silicon wafer 10 rotates at a predetermined speed and at the same time the liquid drop supply arm 20 is drive-controlled by the controller 50 and the liquid drop holder 30 moves in the radius direction A at a predetermined speed (for example, a pitch of several mm per rotation). Thus the liquid drop holder 30 rotates relative to the silicon wafer 10 at a predetermined speed in the circumference direction ω of the silicon wafer 10 while moving at a predetermined speed in the radius direction A of the silicon wafer 10. As a result, as shown in FIG. 4B, the chemicals center 40c is moved on the front plane 10a of the silicon wafer 10 in the circumference direction ω and forms a spiral-shaped trajectory starting from the center 10c of the silicon wafer 10.

If the position in the radius direction of the liquid drop holder 30 reaches a position in which, on the front plane flat part 11 of the silicon wafer 10, the boundary region bordering the chamfered part 15 can contact the liquid drop holder 30, the controller 50 stops the movement of the liquid drop holder 30 in the radius direction A and maintains the position in the radius direction. The relationship of the positions of the silicon wafer 10 and the liquid drop holder 30 at this time is shown in FIG. 8B.

Next the controller 50 rotates the silicon wafer 10 one rotation in a state in which the position in the radius direction A of the chemicals 40 is determined and maintained at a position shown in FIG. 8B. Thus, as shown in FIG. 8A, scanning is performed in the circumference direction ω, while the chemicals center 40c is maintained at the same radius distance R, from a start point S1 to a finish point G1. The chemicals center 40c draws a true circle centered on the wafer center 10c. Thus the impurities on the boundary region bordering the chamfered part 15 on the front plane flat part 11 are dissolved into the chemicals 40. Note that scanning may also be performed two or more times from the start point S1 to the finish point G1, and that scanning may also be performed in which after completing the scan from the start point S1 to the finish point G1, the chemicals center 10c returns to the start point S1 from the finish point G1.

As shown above the chemicals 40 can be completely collected without exception on the entire range of the front plane flat part 11 of the silicon wafer 10. The chemicals collecting region 45 is the complete portion (the front plane flat part 11), with the exception of the chamfered part 15 (shown by the diagonal lines), of the front plane 1a, as shown in FIG. 8A.

The chemicals 40 that dissolved the impurities are collected into the tank 60 carried to the tank 60 while still being retained by the liquid drop holder 30. The degree of contamination of the front plane flat part 11 of the silicon wafer 10 can be evaluated by analyzing the chemicals 40 collected in the tank 60.

As shown above the chemicals 40 completely contact without exception the entire range of the front plane flat part 11 of the silicon wafer 10, hence the analysis and evaluation of the degree of contamination of the front plane flat part 11 can be performed at a highly stable accuracy.

Comparing the present invention with the prior art as shown in FIGS. 5A and 5B, in the prior art the chemicals center 40c forms a spiral-shaped trajectory on its last circuit, thus there is a problem in which the chemicals 40 are not collected on all the portions of the front plane flat part 11, however, according to the first embodiment, the trajectory is formed in a true circle in a state in which the chemicals 40 are retained at a position in which it can contact the boundary region bordering the chamfered part 15, thus the chemicals 40 can be collected from the entire range of the front plane flat part 11.

(Collecting Performed on the Chamfered Part 15)

FIG. 9 is a side view showing the relative positions of the liquid drop holder 30 and the silicon wafer 10 when the chemicals are collected from the chamfered part 15. FIG. 10 is a side view showing the relative positions of the outer portion of the silicon wafer 10 and the chemicals 40.

As mentioned above, when the collecting of the chemicals on the front plane flat part 11 is finished, the controller 50, as subsequently shown in FIG. 9, further moves the liquid drop holder 30 in the radius direction A and at the same time lowers the height of the liquid drop holder 30 and moves the liquid drop holder 30 to a position in which the chemicals 40 can contact both the chamfered part 15 of the silicon wafer 10 and, on the front plane flat part 11, the boundary region 11a bordering the chamfered part 15. Thus, if a state is reached in which the chemicals 40 can contact both the chamfered part 15 and the boundary region 11a then the controller 50 stops the movement of the liquid drop holder 30 in the radius direction A and the height direction H.

Next the controller 50 rotates the silicon wafer 10 one circuit and scans liquid drop center 40c in the circumference direction ω of the silicon wafer 10 in a state in which the position in the radius direction and the height of the liquid drop holder 30 are set to the position and height shown in FIG. 9. Note that scanning may also be performed two or more times, and that scanning may also be performed in which after completing the scan from the start point to the finish point the liquid drop center 10c returns to the start point from the finish point.

Thus, as shown in FIG. 10, the chemicals 40 span the entire region in the circumference direction of the silicon wafer 10, and contacts both the chamfered part 15 and the boundary region 11a (the chemicals collecting region 46), and the impurities adhered to the chamfered part 15 are dissolved into the chemicals 40. At this point the impurities adhered to the boundary region 11a have already been collected through the last collecting step of the front plane flat part 11 shown in FIG. 8A. Accordingly, the impurities on the boundary region 11a do not mix into the chemicals 40 even if a portion of the chemicals 40 is in contact with the boundary region 11a as in FIG. 10, and only the impurities adhered to the chamfered part 15 dissolve into the chemicals 40.

The chemicals 40 in which impurities are dissolved are collected into the tank 60 carried to the tank 60 while still being retained by the liquid drop holder 30. By analyzing the chemicals 40 collected in the tank 60 the degree of contamination on the chamfered part 15 of the silicon wafer 10 can be evaluated.

As shown above, only the impurities on the chamfered part 15 of the silicon wafer 10 are dissolved into the chemicals 40, hence the analysis and evaluation of the degree of contamination of the chamfered part 15 can be performed with great accuracy.

Comparing the present invention with the prior art as shown in FIG. 7, in the prior art a method is employed in which the silicon wafer 10 is placed in a perpendicular position and dipped into the chemicals 40, hence impurities on the back plane flat part 16 and the front plane flat part 11, or impurities that have fallen from above, are mixed into the chemicals 40, thus the analysis and evaluation of the degree of contamination of the chamfered part 15 cannot be performed with good accuracy, however, in the first embodiment the chemicals 40 contact only the chamfered part 15 and the boundary region 11a (the chemicals collecting region 46), however, since the impurities have already been collected from the boundary region 11a, only the impurities on the chamfered part 15 are taken into the chemicals 40 and the analysis and evaluation of the degree of contamination are performed with great accuracy.

Next the composition of the chemicals 40 will be described.

As shown in FIG. 9 since the chemicals 40 are reached into the chamfered part 15 from the front plane flat part 11, it is desirable that the composition of the chemicals 40 is such that its adhesion to the silicon wafer 10 is high.

The adhesion of the chemicals 40 can be increased by raising the viscosity and the oxidative property of the chemicals 40. In other words, the adhesion can be raised by raising the viscosity of the chemicals 40. Also, the hydrophilic property can be increased and the adhesion raised by increasing the oxidative property of the chemicals 40.

In an experiment a prepared aqueous solution of the chemicals 40 formed from fluorine and nitric acid was used to obtain a viscosity in which the chemicals 40 can be reached into the chamfered part 15 from the front plane flat part 11 side, as shown in FIG. 9. Thus, a good adhesion is obtained.

Second Embodiment

In the first embodiment described above, when chemicals collecting is performed on the front plane flat part 11, as shown in FIG. 4B, the chemicals 40 are caused to scan in the circumference direction while being moved at a fixed speed in the radius direction A as far as the boundary region bordering the chamfered part 15, thus forming a spiral-shaped trajectory.

However, a true circle trajectory may also be formed by causing movement at a predetermined pitch in the radius direction after scanning has been performed in the circumference direction for one or more rotations in a state in which the position of the liquid drops 40 is fixed in the radius direction, and by repeatedly performing an operation that causes scanning to be performed in the circumference direction in the same state in which the position of the liquid drops 40 is fixed in the radius direction. If chemicals collecting is performed without exception on the entire range of the front plane flat part 11 then there is no reason that the trajectory of the chemicals 40 (chemicals center 40c) should be limited to the spiral shape shown in FIG. 4B.

Third Embodiment

In the first and the second embodiments described above, the chemicals 40 scan the entire surface of the front plane flat part 11 (FIG. 4B, FIG. 8A), then the scanning of the chamfered part 15 (FIG. 9) is performed, however, if the analysis and evaluation of the degree of contamination of the front plane flat part 11 is not required and analysis and evaluation of the degree of contamination is only performed on the chamfered part 15, then scanning of the chemicals 40 on the entire surface of the front plane flat part 11 is not always necessary, and it is possible to omit the scanning shown in FIG. 4B and scan, on the front plane flat part 11, only the boundary region bordering the chamfered part 15 as shown in FIG. 8A, and then perform the scanning (FIG. 9) of the chamfered part 15.

The third embodiment process will be explained.

At first the chemicals center 40c is positioned, not at the wafer center 10c, but at the start point S1 as shown in FIG. 8A, then scanning is begun from the start point S1 and continued in the circumference direction ω to the finish point G1. Thus the chemicals 40 only contact, on the front plane flat part 11, the boundary region bordering the chamfered part 15, and the impurities are dissolved into the chemicals 40. Then the chemicals 40 with impurities dissolved therein are collected into the tank 60. Next scanning (FIG. 9) of the chamfered part 15 shown in FIG. 9 is preformed. The chemicals 40 contact the chamfered part 15 and the boundary region 11a and the impurities are dissolved into the chemicals 40. Then the chemicals 40 with impurities dissolved therein are collected into the tank 60. The degree of contamination of the chamfered part 15 of the silicon wafer 10 is evaluated by analyzing the chemicals 40 collected into the tank 60.

In this third embodiment also, the chemicals 40 contact both the chamfered part 15 and the boundary region 11a (the chemicals collecting region 46), as shown in FIG. 10, however, since the impurities adhered to the boundary region 11a have already been collected by scanning of the chemicals 40 on, on the front plane flat part 11 as shown in FIG. 8A, the boundary area of the chamfered part 15, the impurities on the boundary region 11a are not mixed into the chemicals 40, and only the impurities adhered to the chamfered part 15 are taken in by the chemicals 40, and the analysis and evaluation of the degree of contamination of the chamfered part 15 of the silicon wafer 10 can be performed with good accuracy.

Fourth Embodiment

The chemicals collecting region 46 of the chamfered part 15 may be a region that spans the entire periphery of the silicon wafer 10 and may also be a region that is a portion of a circular arc in the circumference direction of the silicon wafer 10.

For example as shown in FIG. 11A, it is also possible to set the start point S2 and the finish point G2 of the collecting at a desired point (angle) on the silicon wafer 10, and collect the chemicals 40 on the region 46 from this start point S2 to this finish point G2. The start point S2 can be set at a position removed from the position of a notch 17.

Next the fourth embodiment process will be explained.

The chemicals center 40c is scanned in the circumference direction ω to the finish point G1 as shown in FIG. 8A. The finish point G1 is set so that the position on the periphery (the angle of rotation) conforms to the collecting start point S2 of FIG. 11A. Thus the chemicals 40 contact the front plane flat part 11 and the impurities are dissolved into the chemicals 40. Then the chemicals 40 with the impurities dissolved therein are collected into the tank 60.

When the scanning of the front plane flat part 11 shown in FIG. 8A is finished, the chemicals center 40c is caused to move in the radius direction A, to the collecting start position S2, while maintaining the position of the chemicals center 40c on the periphery (the angle of rotation) (G1), and then maintained in the state shown in FIG. 9. Then the chemicals center 40c is scanned in the circumference direction ω to the collecting finish point G2, and chemicals collecting is performed on the chamfered part 15 on the region 46 from the start point S2 to the finish point G2 as shown in FIG. 11B. The positions of start point S2 and finish point G2 on the periphery can be replaced with the angle of rotation of the silicon wafer 10. For example, a sensor is provided which detects the current angle of rotation of the silicon wafer 10 and the detection results of the sensor is fed back to the controller 50. The controller 50 controls the rotation of the silicon wafer 10 in order for the chemicals center 40c to move from the start point S2 (the start angle of the rotation) to the finish point G2 (the finish angle of rotation), on the basis of the fed back angle of rotation of the wafer.

Thus the chemicals 40 contact the chamfered part 15 and the boundary region 11a and the impurities are dissolved into the chemicals 40. Then the chemicals 40 with impurities dissolved therein are collected into the tank 60. Then the degree of contamination of the chamfered part 15 of the silicon wafer 10 is evaluated by analyzing the chemicals 40 collected into the tank 60.

In this fourth embodiment also, the chemicals 40 contact both the chamfered part 15 and the boundary region 11a (the chemicals collecting region 46), as shown in FIG. 10, however, since the impurities adhered to the boundary region 11a have already been collected by the chemicals 40 scanning, on the front plane flat part 11, the boundary region bordering the chamfered part 15, as shown in FIG. 8A, the impurities on the boundary region 11a are not mixed into the chemicals 40 and only the impurities adhered to the chamfered part 15 are taken into the chemicals 40, and the analysis and evaluation of the degree of contamination of the chamfered part 15 of the silicon wafer 10 can be performed accurately.

Furthermore, according to the fourth embodiment, the chemicals collecting region is not limited to the region 44 in which it is possible to verify the angle by sight, as in the prior art (FIG. 11B), hence the start point S2 and the finish point G2 can be set as desired and collecting can be performed on a desired region 46, thus the degree of flexibility in indicating the chemicals collecting region is improved. For example, the specified chemicals collecting region, such as the location in which the silicon wafer 10 is fastened, can be indicated with pinpoint precision and the evaluation of the degree of contamination of the specified region 46 can be performed.

Note that in the fourth embodiment, since the chemicals collecting of the chamfered part 15 is limited to a portion of a circular arc on the periphery, as shown in FIG. 11A, when scanning is performed on the boundary region bordering the chamfered part 15 as in FIG. 8A, scanning may only be performed on the inner portion of the circular arc shaped region corresponding to the region 46 in FIG. 11A.

As explained above, according to the exemplary embodiment, since the impurities outside of the chamfered part 15 are not mixed into the chemicals 40, the analysis and evaluation of the degree of contamination of the chamfered part 15 can be performed accurately.

Also according to the exemplary embodiment, there is a dramatic improvement in the operation efficiency due to being able to perform in succession chemicals collecting on both the front plane flat part 11 and the chamfered part 15 using one liquid drop automatic scanning device (FIGS. 1A and 1B) and one silicon wafer 10.

Note that the operation explained in the exemplary embodiment can be realized by changing the control program in the controller 50 of liquid drop automatic operation devices already in existence. A simple conversion is employed in which a program, in which the control programming is changed so the liquid drop holder 30 is moved in the radius direction A and the height direction H, is installed in the controller 50, hence the costs necessary in developing these devices can be dramatically reduced. Note that in the exemplary embodiment, the silicon wafer 10 is rotated and scanning is carried out with the liquid drop holder 30 in the circumference direction ω, however, scanning may be carried out with the liquid drop holder 30 in the circumference direction ω by rotating the liquid drop supply arm 20 instead of rotating the silicon wafer 10. In the same manner relative movement in the radius direction A in relation to the silicon wafer 10 of the liquid drop holder 30 may be carried out by moving the silicon wafer 10 instead of moving the liquid drop supply arm 20.

Also according to the exemplary embodiment the degree of flexibility in specifying the chemicals collecting region is improved since the collecting start point and the collecting finish point can be set as desired and a desired region can be collected when collecting the chemicals 40 on the chamfered part 15.

Fifth Embodiment

In the exemplary embodiments described above the explanation was made assuming a case in which chemicals collecting is performed on the chamfered part 15, however, in the case in which the analysis and evaluation of the degree of contamination of the chamfered part 15 is unnecessary and only the analysis and evaluation of the degree of contamination of the front plane flat part 11 is performed, the step may be finished after the scanning of, on the front plane flat part 11, the boundary region bordering the chamfered part 15, as shown in FIG. 8A and the collecting of the chemicals 40 in the tank 60 are finished, without continuing to the scanning of the chamfered part 15 shown in FIG. 9. According to the fifth embodiment, the chemicals 40 can be, without exception, collected from the entire range of the front plane flat part 11, hence the analysis and evaluation of the degree of contamination of the front plane flat part 11 can be performed accurately.

INDUSTRIAL APPLICABILITY

In the exemplary embodiments explanations were made concerning a silicon wafer, however, semiconductor wafers besides silicon wafers, for example gallium arsenide wafers can also be processed in the same manner.

Figure 1A:
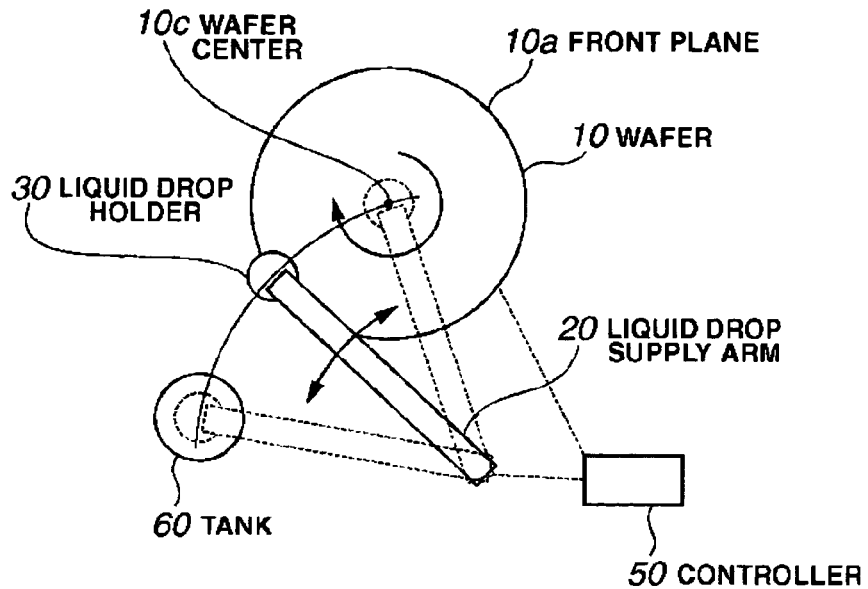
FIGS. 1A and 1B are drawings showing a structure of a liquid drop automatic scanner.
Figure 1B:
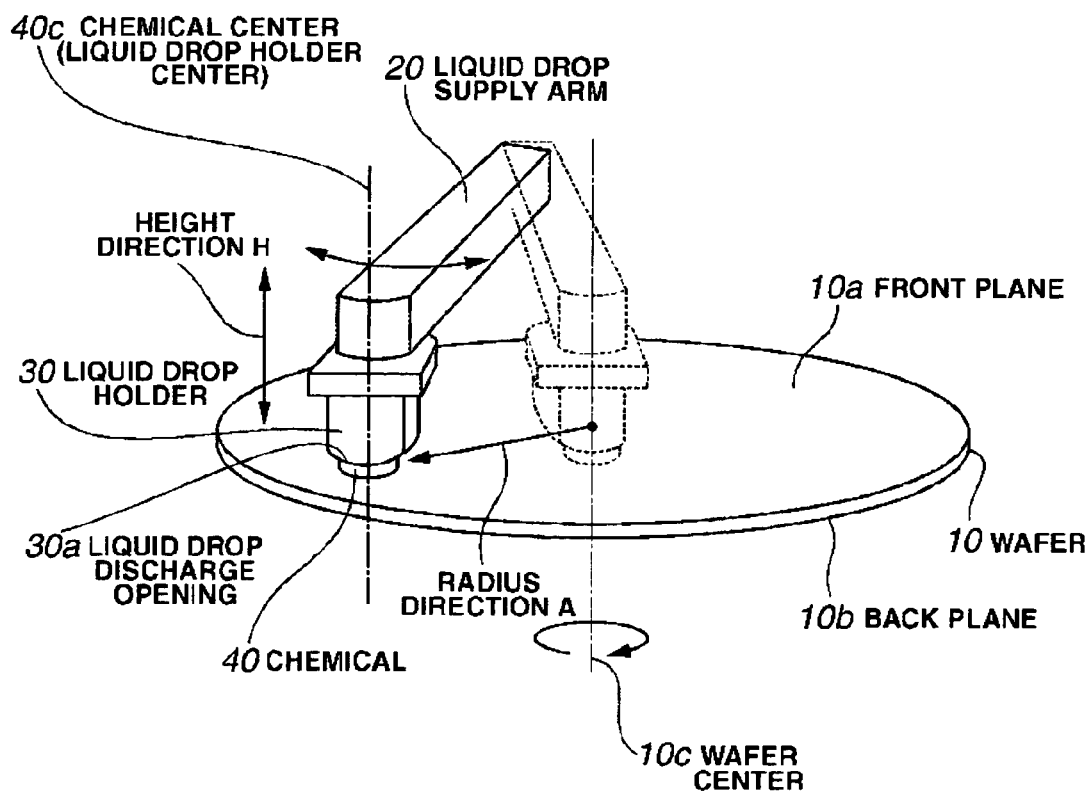
Figure 2A:
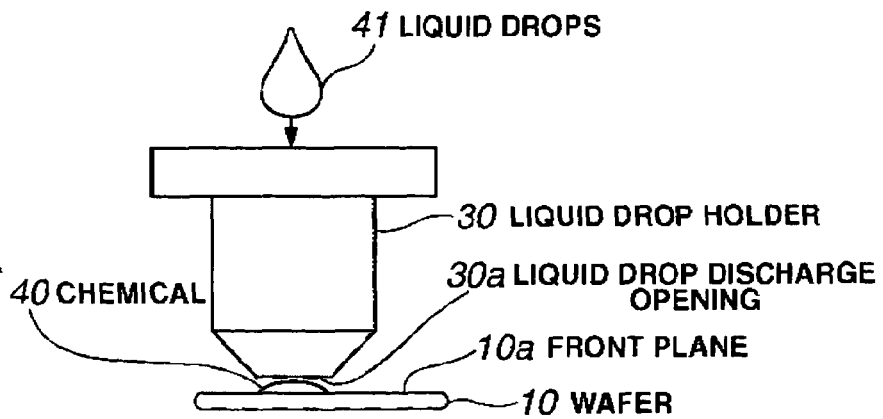
FIGS. 2A to 2D are drawings explaining a operation of a liquid drop holder, which retains chemicals.
Figure 2B:
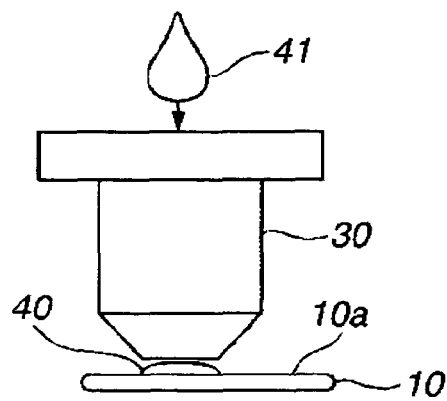
Figure 2C:
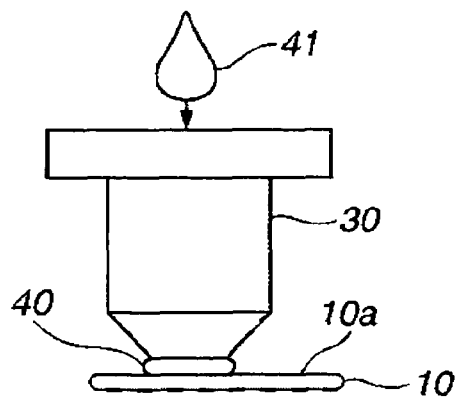
Figure 2D:
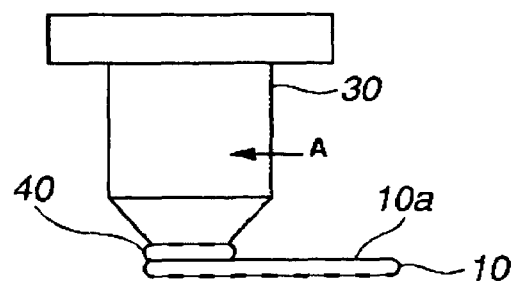
Figure 3:
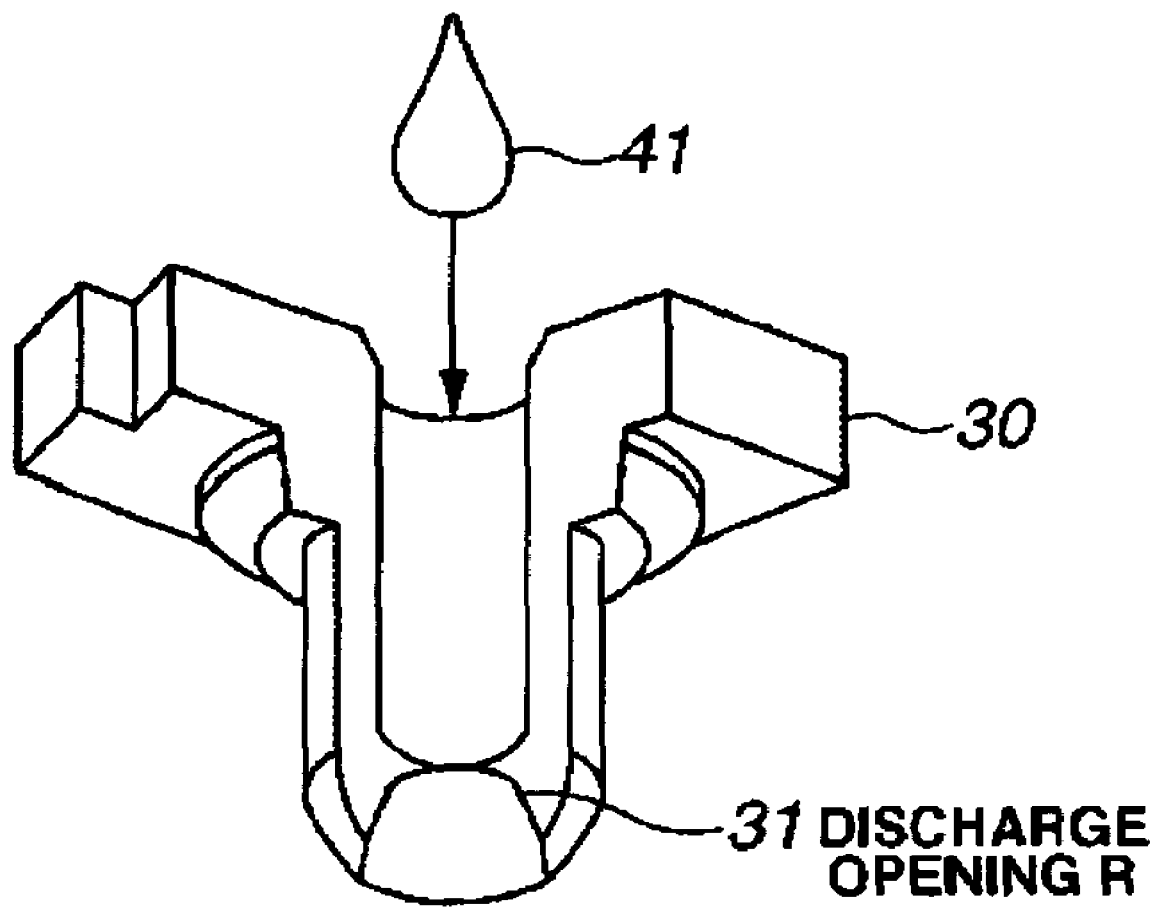
FIG. 3 is a perspective drawing showing an inner portion of the liquid drop holder.
Figure 4A:
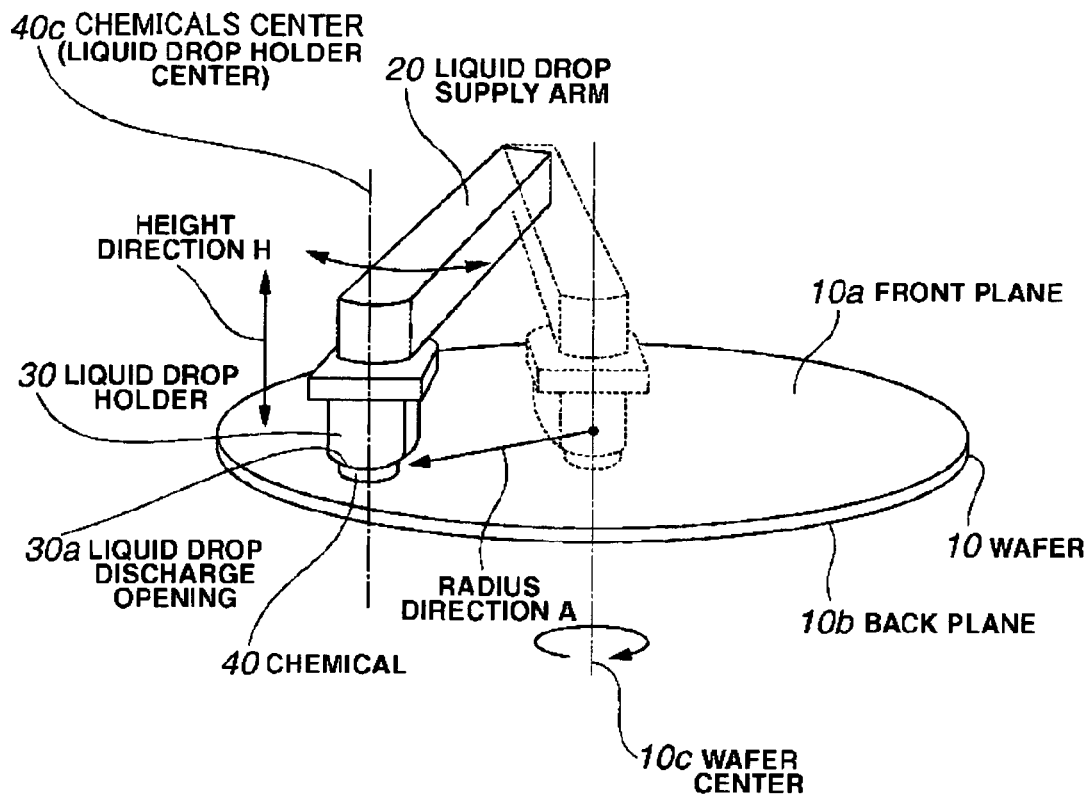
FIGS. 4A and 4B are drawings explaining movement of a chemicals center in relation to a silicon wafer.
Figure 4B:
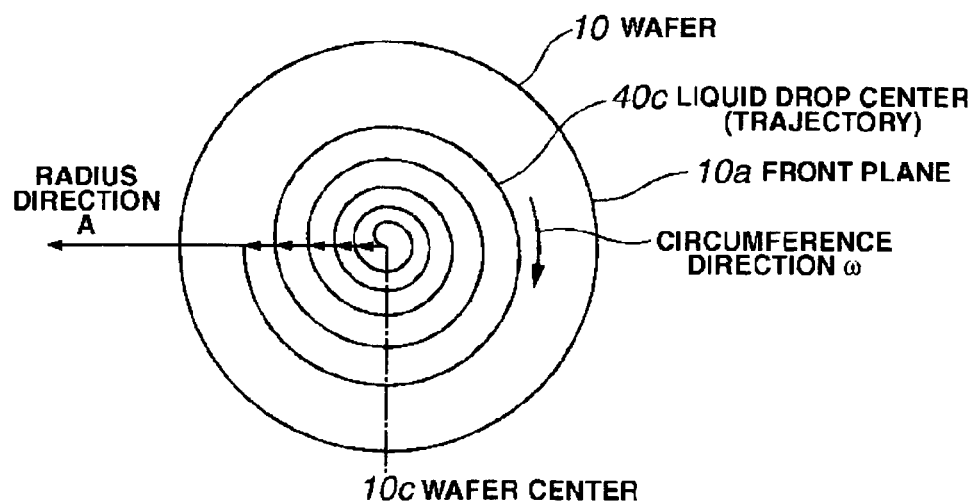
Figure 5A:
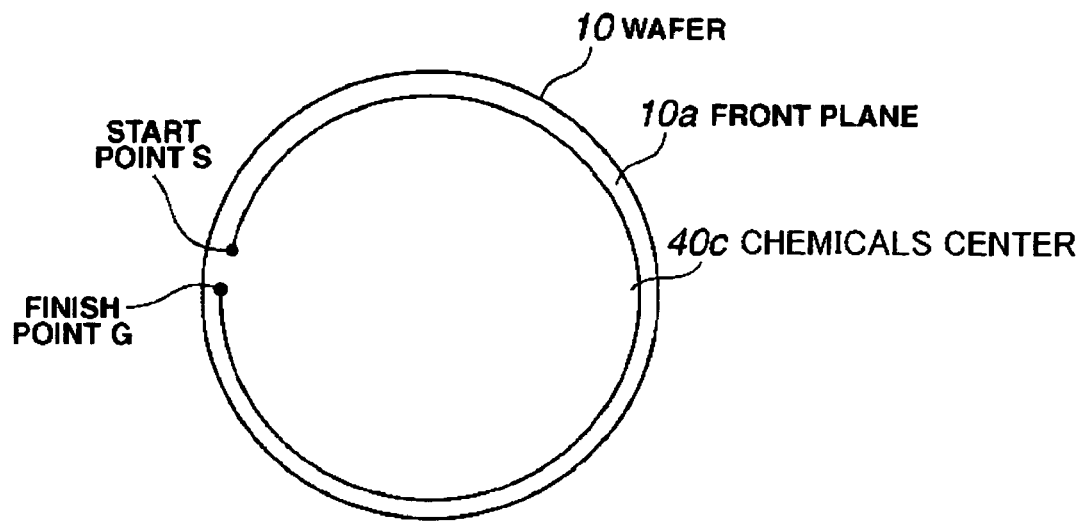
FIGS. 5A and 5B are drawings explaining a movement of the chemical center in relation to the silicon wafer in the prior art.
Figure 5B:
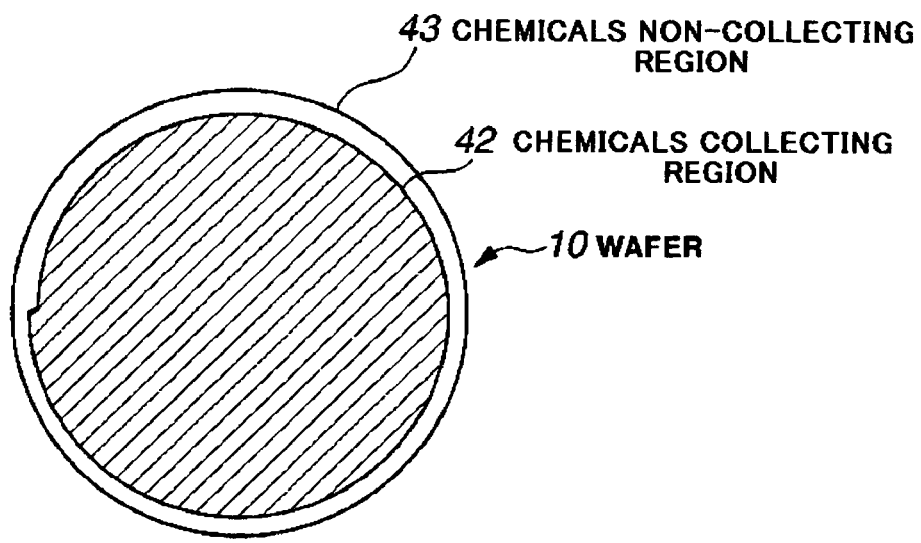
Figure 6:
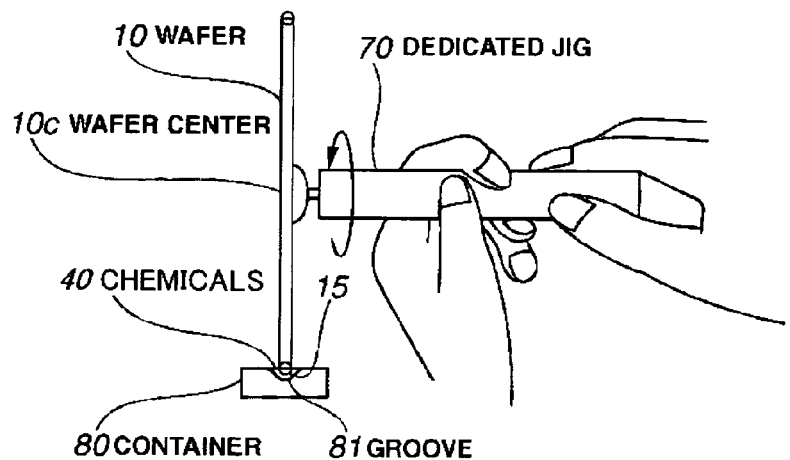
FIG. 6 is a drawing explaining an operation of a manual liquid drop collecting device in the prior art.
Figure 7:
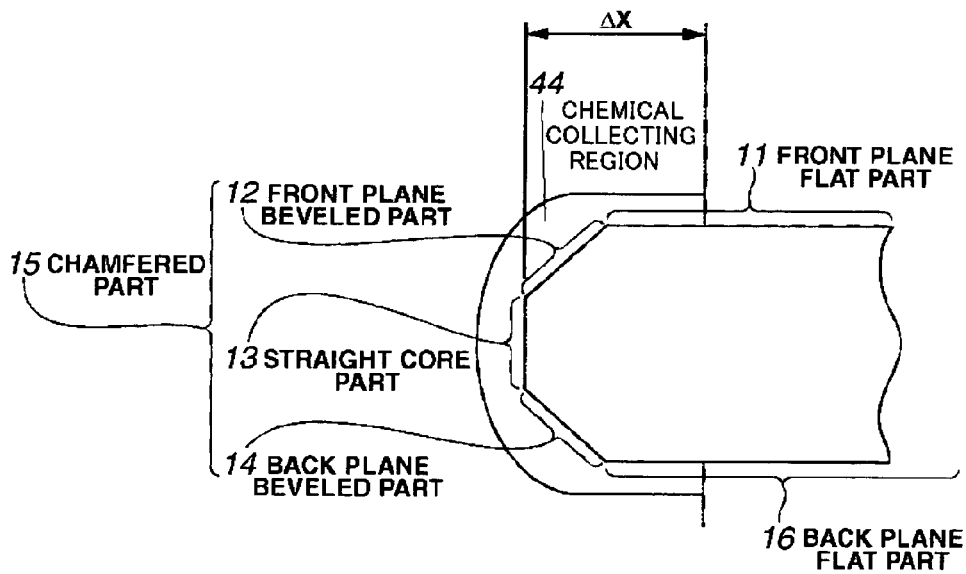
FIG. 7 is a drawing showing a collecting region of the manual liquid drop collecting device of FIG. 6.
Figure 8A:
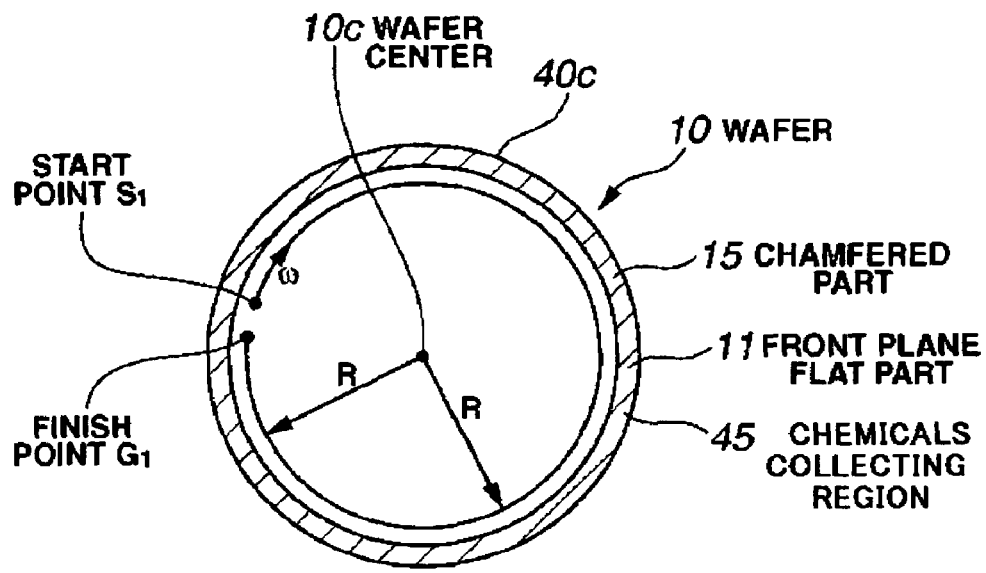
FIGS. 8A and 8B are drawings explaining the scanning operation in a circumference direction in a state in which a position is determined in a radius direction in which the chemical can contact, on the front plane flat part, a boundary region bordering a chamfered part.
Figure 8B:
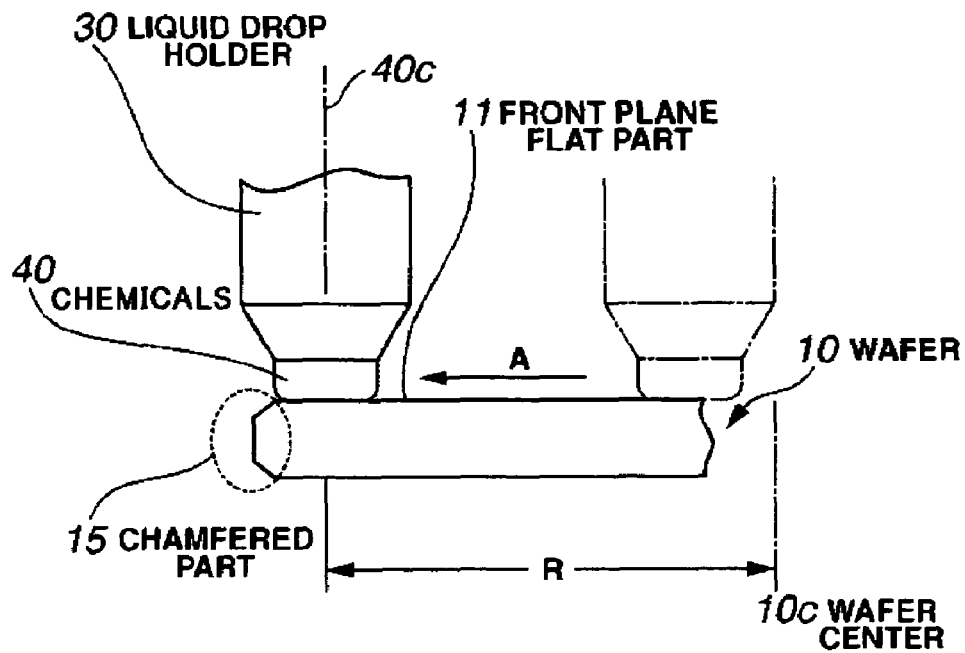
Figure 9:
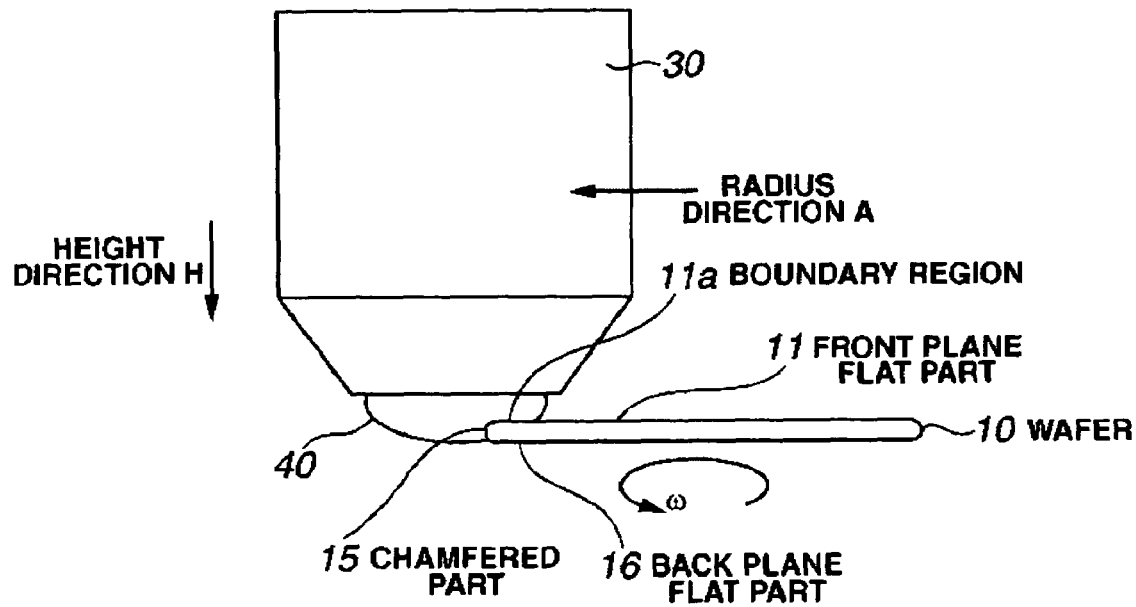
FIG. 9 is a drawing showing the state in which the chemicals can contact both the chamfered part and, on the front plane flat part, the boundary region bordering the chamfered part.
Figure 10:
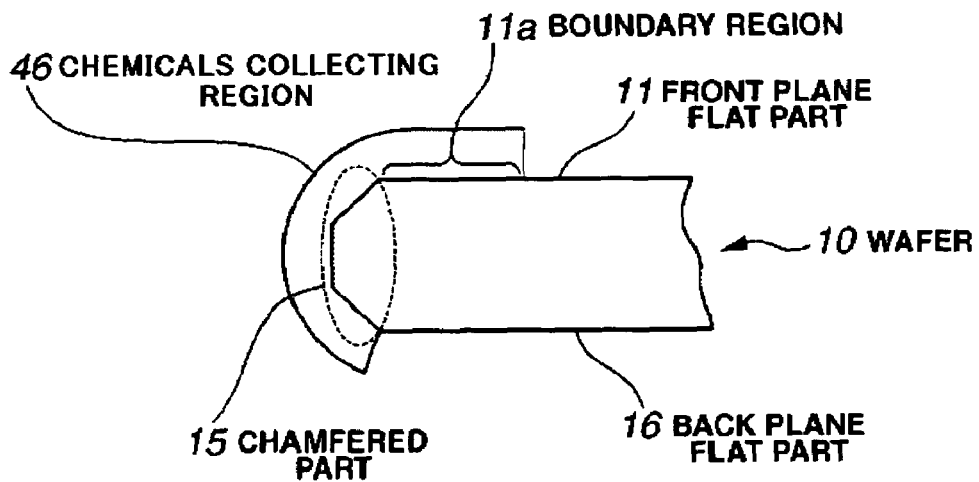
FIG. 10 is a drawing showing the chemicals collecting region when the position is determined in the state shown in FIG. 9.
Figure 11A:
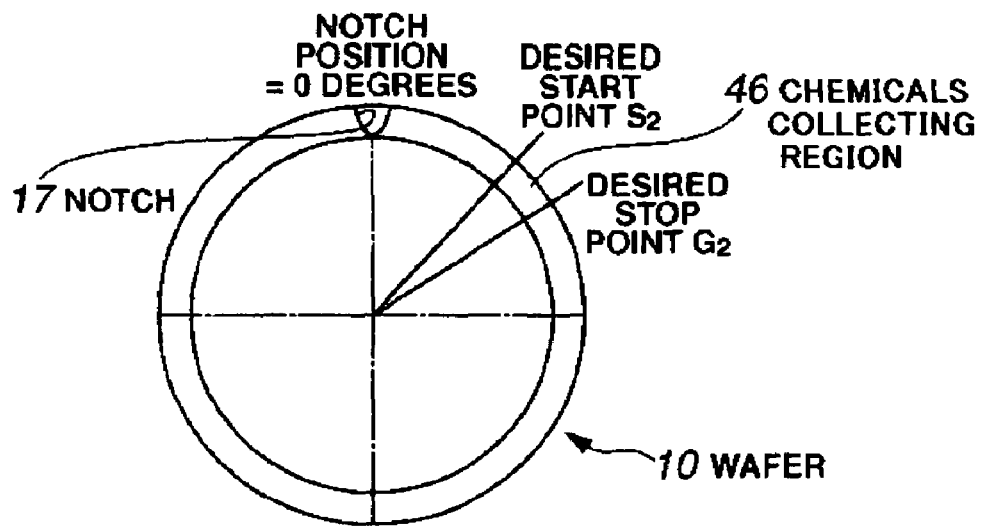
FIG. 11A is a drawing showing the chemicals collecting region in which collecting is possible in the exemplary embodiment.
Figure 11B:
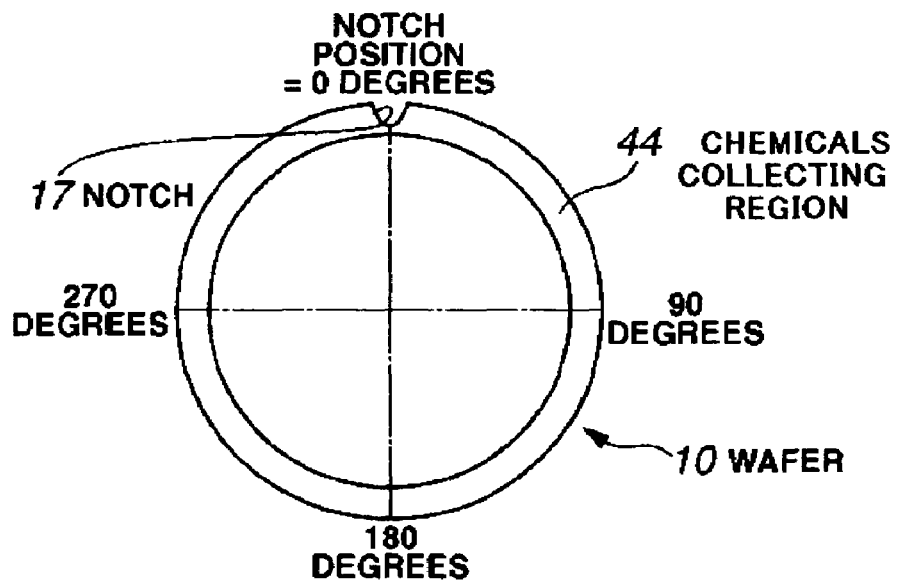
FIG. 11B is a drawing showing the chemicals collecting region in which collecting is possible in the prior art.

The invention claimed is:

1. A method of collecting impurities from a semiconductor wafer, in which impurities are removed from the wafer's surface by moving a liquid drop relative to the surface of the wafer so as to dissolve impurities into the liquid drop, the method comprising;

forming a liquid drop on the surface of the wafer;

holding the liquid drop with a liquid drop holder that can move the drop across the surface of the wafer;

a first scanning step of scanning in the circumference direction while causing the drop to move radially from the center of the wafer to, on a front plane flat part of the semiconductor wafer, a boundary region bordering a chamfered part;

a second scanning step of fixing the drop at a radial position where the drop can contact the boundary region bordering the chamfered part, and scanning in the circumference direction;

a first collecting step of collecting the drop that includes dissolved impurities that were removed from the front plane flat part of the semiconductor wafer;

a third scanning step of positioning the liquid drop holder at a position where a drop held by the drop holder can contact both the chamfered part and boundary region of the semiconductor wafer, fixing the held drop at the radial position where the drop can contact both the chamfered part and the boundary region, and scanning in the circumference direction so that impurities on the chamfered part can be dissolved into the held drop; and a second collecting step of collecting the drop that includes impurities that were removed from the chamfered part of the semiconductor wafer, said second collecting step being separate from said first collecting step.

* * * * *